United States Patent [19]

Saab

[11] Patent Number: 5,246,421
[45] Date of Patent: Sep. 21, 1993

[54] METHOD OF TREATING OBSTRUCTED REGIONS OF BODILY PASSAGES

[76] Inventor: Mark A. Saab, 396 Andover St., Lowell, Mass. 01852

[21] Appl. No.: 834,602

[22] Filed: Feb. 12, 1992

[51] Int. Cl.⁵ ............................................. A61M 29/02
[52] U.S. Cl. ..................................... 604/96; 606/194; 128/898
[58] Field of Search ........................... 604/96–101, 604/271; 606/191, 192, 194; 128/898

[56] References Cited

U.S. PATENT DOCUMENTS

| | | |
|---|---|---|
| Re. 32,983 | 7/1989 | Levy . |
| 1,852,351 | 4/1932 | Lewis . |
| 4,299,226 | 11/1981 | Banka . |
| 4,422,447 | 12/1983 | Schiff . |
| 4,540,404 | 9/1985 | Wolvek . |
| 4,564,014 | 1/1986 | Fogarty et al. ............... 606/194 |
| 4,655,746 | 4/1987 | Daniels et al. ............... 604/101 |
| 4,681,092 | 7/1987 | Cho et al. . |
| 4,820,349 | 4/1989 | Saab . |
| 4,863,440 | 9/1989 | Chin ........................... 606/194 |
| 5,074,845 | 12/1991 | Miraki et al. ............... 604/101 |
| 5,078,725 | 1/1992 | Enderle et al. .............. 604/96 |

FOREIGN PATENT DOCUMENTS 9104763  4/1991  World Int. Prop. O. .......... 606/194

Primary Examiner—C. Fred Rosenbaum
Assistant Examiner—William Lewis
Attorney, Agent, or Firm—Schiller & Kusmer

[57] ABSTRACT

An adjustable-length balloon dilatation catheter apparatus and a method for using the same are disclosed wherein an adjustable sheath is externally manipulated to partially surround and contain the dilatation balloon segment of the catheter while the catheter and balloon segment are in situ during a treatment procedure. By sliding the sheath forward or backward to expose a predetermined length of the balloon segment prior to inflating the balloon, the catheter apparatus of this invention is useful in medical procedures requiring balloons of varying lengths.

17 Claims, 2 Drawing Sheets

METHOD OF TREATING OBSTRUCTED REGIONS OF BODILY PASSAGES

The present invention relates generally to balloon catheters and, more particularly, to catheters provided with adjustable length balloons.

BACKGROUND OF THE INVENTION

The use and construction of balloon catheters is well known in the art. It is also well known to either attach a balloon segment adhesively to the end of a catheter or, alternatively, the balloon can be formed integrally with the catheter Such balloon catheters are described in U.S. Pat. No. Re. 32,983 to Levy and U.S. Pat. No. 4,820,349 to Saab.

It is also well known in the art to use balloon catheters in combination with guide catheters that assist in properly positioning the balloon catheter inside the body. Typically, the guide catheter is of a more rigid and durable construction than the balloon catheter. It may also have smooth, slippery or low friction surfaces to facilitate its movement through a lumen, such as a blood vessel, without causing trauma or tissue damage, until the distal end of the guide catheter is within a preselected distance, e.g., about 10 cm. or so, of the selected treatment area. The smaller diameter balloon catheter can then be threaded through the guide catheter until the balloon segment of the balloon catheter emerges from the distal end of the guide catheter proximate to the intended treatment site.

Alternatively, the balloon catheter can be positioned inside the guide catheter prior to insertion of the guide catheter into the body lumen, e.g., the blood vessel. In this procedure, once the distal end of the guide catheter is proximate to the selected treatment area, the balloon catheter is moved forward until all of the balloon segment has cleared the distal end of the guide catheter and is positioned at the intended treatment site.

Present balloon catheter technology employs balloons of fixed diameter and length. There are many medical procedures which employ balloon catheters which require a prior determination of the necessary length of the balloon in order to carry out the procedure. For example, in balloon angioplasty, the length of the diseased blood vessel is first determined. Usually, the surgeon determines in advance, for example through fluoroscopic X-ray, ultrasound, and/or CAT scanning techniques, the approximate size of the area to be treated. Where only one length balloon is available (usually predetermined so that it will be, in most instances the size, and therefore usually shorter than the length of many diseased portions of blood vessel encountered in balloon angioplasty procedures) the surgeon will sequentially dilate different portions of the vessel extending the time and risks of the procedure. Where several catheters of differing balloon lengths are available, based upon observations by the surgeon, the surgeon will select a balloon length which will cover the entire length of the portion of the vessel requiring dilatation. If two or more blockage sites of different sizes exist within the same artery and the attending physician determines that two or more different sized balloons should be used, the surgeon may have to treat the most proximate site first, deflate and withdraw the first balloon catheter, and then insert a second balloon catheter having a balloon segment of a size commensurate with the size or location of the second obstruction or stenotic region that is going to be treated. Shorter balloons are often used to dilate lesions located on sharp bends in coronary arteries to prevent straightening and possible damage during the dilatation procedure. Longer balloons are employed to dilate large areas with extensive disease. Changing balloons, however, is a costly, time-consuming and potentially risky procedure that could lead to injury or death of the patient.

In addition, while it is believed the greatest use for balloon catheters is for treating profuse disease in blood vessels, and in particular diseased portions of peripheral and coronary arteries, there are certain other procedures where one of a plurality of catheters having different length balloons must be selected. For example, at least one prostate dilatation procedure requires the measurement of the prostate. The size of the balloon is the selected depending on the size of the prostate for which the procedure is being performed.

Thus, in the foregoing procedures, the surgeon must have catheters with various sized balloons on hand so that he can select the proper size balloon when performing the procedure.

Representative of the prior art in this field is U.S. Pat. No. 4,299,226 to Banka. The Banka patent discloses a method of dilating coronary arteries using a balloon-type catheter. The first step in the Banka method is to insert a "single lumen guide catheter 100 . . . so that the tip is positioned . . . within at least 20 cm., and preferably with (sic) 10 cm. of the blockage 300 to the dilated," (col. 3., lines 19-24 and FIG. 3). The second step in Banka is to thread a "double lumen balloon catheter 200 ... through the single lumen 101 of that guide catheter," (col. 3, lines 29-34 and FIG. 3). The result is that the dilation balloon 204 passes completely along the inside length of guide catheter 100 to emerge from the distal end of guide catheter 100 at a point within a predetermined distance from the arterial obstruction or stenotic region to be dilated. There is no suggestion in Banka that guide catheter 100 could be positioned or manipulated so as to prevent a portion of balloon 204 from dilating when in use.

U.S. Pat. No. 4,540,404 (Wolvek) is directed to a balloon catheter apparatus comprising a tapered distal end 12, a central lumen 38, and a balloon membrane 26 coaxial with and surrounding the central lumen and connected to the tip (FIG. 2A). According to the description in this patent, "a sheath 30 is slidable over the balloon to form an assembly . . . The sheath fits loosely over the balloon, whereby the sheath can be withdrawn to expose the balloon at the selected location and the balloon can then be inflated to provide therapy," (Abstract; FIG. 4). Furthermore, according to Wolvek, "Sheath 30 is sufficiently rigid to prevent the longitudinal collapse of the balloon membrane 26 as the (intraaortic balloon) IAB 10 is inserted into the body and advanced along the artery," (col. 3, lines 65-68).

As in the Banka patent, there is no suggestion in Wolvek that sheath 30 could be positioned or manipulated so as to prevent a portion of balloon membrane 26 from dilating when in use. On the contrary, at col. 4, lines 52-55 and again at col. 5, lines 36-36, Wolvek states that, before dilation of the balloon, sheath 30 is withdrawn so that balloon membrane 26 is "completely uncovered". Furthermore, the frustoconical configuration of distal end 12, including a base portion 22 which "constitutes a shoulder facing in the proximal direction" (col. 4, lines 8-9 and FIG. 2A), "prevents the sheath 30 from overriding the distal end 18 of the tip 12 when pushed thereagainst . . . " (col. 4, lines 14-16). Thus, the Wolvek configuration restricts movement of sheath 30 in the distal direction.

U.S. Pat. No. 4,422,447 (Schiff) and U.S. Pat. No. 4,681,092 (Cho et al.) are directed to intra-aortic balloon catheters and to devices for "wrapping" the balloon portions prior to insertion of the catheters into the artery. In each of these patents, a sheath or sleeve portion (Schiff, FIG. 3, sheath 40; Cho et al., FIG. 6, sheath 56) is used to facilitate introduction of the balloon catheter into the artery.

The principal function of the sheath or sleeve portions in these patents appears to be maintaining the balloon sections in a tight, wrapped condition until the balloon sections are guided through the artery to the point of treatment. But, once the balloon section is delivered to the proper arterial location, the sheath or sleeve must be retraced (or the balloon must be advanced beyond the distal end of the sheath) such that the balloon section is completely uncovered and free to unwrap and dilate. If the sheath at this point continued to cover any part of the wrapped balloon, the balloon could not be fully or properly unwrapped and dilated for treatment purposes.

U.S. Pat. No. 1,852,351 (Lewis) is directed to a vaginal douche pipe comprising an external pipe 1, that serves as a housing and a control for an internal pipe 2 and for a soft, collapsible bulb 3. As illustrated in FIG. 3, during insertion of the apparatus into the vaginal canal, internal pipe 2, with deflated bulb 3 attached at its distal end, is housed inside external pipe 1. After insertion, internal pipe 2 is pushed forward thus permitting bulb 3 to be inflated unconstrained by external pipe 1 (See FIG. 4).

There is no suggestion in Lewis, however, that external pipe 1 could be positioned or manipulated so as to prevent a portion of bulb 3 from inflating. On the contrary, at col. 4, lines 99-107, Lewis states that the device is only ready to use when "internal pipe 2 is pushed forward . . . until the stock of stop cock of valve 4 reaches the right and left side slots . . . which retains . . . bulb 3 in an extended position as shown in FIGS. 2 and 4 . . . ".

These and other problems with and limitations of the prior art balloon dilatation catheters are overcome with the adjustable-length balloon catheters of this invention. Specifically, this invention obviates the need for catheter makers to produce multiple length balloons.

OBJECTS OF THE INVENTION

It is a general object of the present invention to substantially reduce or overcome the above-noted problems of the prior art.

It is a principal object of this invention to provide a balloon dilatation catheter apparatus wherein the length or the shape of the inflated portion of the balloon can be readily adjusted to suit different applications.

It is also an object of this invention to provide a balloon dilatation catheter apparatus comprising coaxial adjustable sheath means dimensioned so as to fit over and around and slide relative to the balloon when the balloon is not inflated.

A further object of this invention is to provide a balloon dilatation catheter apparatus comprising coaxial adjustable sheath means at the distal end thereof for controlling the portion of balloon to be inflated and means for manipulating the sheath means relative to the balloon.

Another object of this invention is to provide a balloon catheter apparatus with coaxial slidable sheath means having sufficient flexibility and tractability to facilitate guiding the sheath means to the treatment site, but also resistance to inflation and rupture greater than that of the balloon.

Still another object of this invention is to provide a method for readily adjusting the length or shape of the inflated portion of the balloon of a balloon catheter such that a single catheter can be used for multiple applications in treating sites of varying sizes and locations.

Other objects of the invention will in part be obvious and will in part appear hereinafter. The invention accordingly comprises the apparatus possessing the construction, combination of elements, and arrangement of parts which are exemplified in the following detailed disclosure, and the scope of the application of which will be indicated in the claims.

SUMMARY OF THE INVENTION

The catheter apparatus of this invention comprises a balloon catheter designed so that the length of the portion of the balloon that is inflatable can be adjusted. The balloon is made sufficiently long so as to accommodate all of the proposed size balloons that might be required for a particular application. An adjustable sheath (in the form, for example, of a slidable sleeve or an independent guide catheter) is provided over the catheter and balloon so that, by manipulating the sheath to the appropriate position so as to cover the unneeded portion of the balloon, only the exposed portion of the balloon will fully inflate when fluid is provided to the balloon. Thus, the sheath must be sufficiently strong and non-compliant so as to prevent the portion of the balloon still covered by the sheath from completely expanding. By sliding the sheath forward or backward with respect to the balloon, part or all of the balloon can be exposed for inflation. In addition, or alternatively, the cross sectional shape and/or dimensions of the balloon can vary along its axial length, and the appropriate section of balloon selected depending upon the particular application. For example, the balloon diameter can also be tapered along its length so that a large area can be dilated even if the diameter of the diseased portion of the blood vessel changes along its length, as is often the case with diseased coronary arteries. This invention thus obviates the need for a multiplicity of catheters fitted with balloons of varying lengths and/or cross sectional shapes or dimensions so as to accommodate different medical applications. Means can be provided for determining the exposed length of balloon.

BRIEF DESCRIPTION OF THE DRAWINGS

For a fuller understanding of the nature and objects of the present invention, reference should be had to the following detailed description taken in connection with the accompanying drawings wherein.

DETAILED DESCRIPTION OF THE INVENTION

Figure 1:
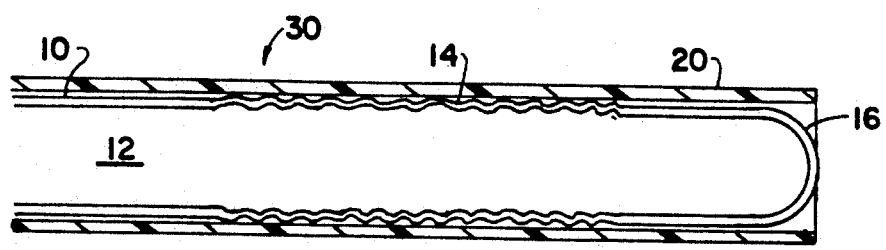
FIG. 1 is a cross-sectional view of an adjustable length balloon catheter apparatus designed in accordance with this invention, wherein the adjustable sheath is shown as completely surrounding the distal end of the catheter including the balloon segment.

FIG. 1 shows a cross-sectional view of the distal end of a balloon dilatation catheter apparatus 30 comprising a catheter body 10 defining a lumen 12, a balloon 14, and a catheter tip 16 The catheter body 10 is shown as an integral one piece assembly, having a closed end, such designs being described in my co-pending application, U.S. patent application Ser. No. 07/522,178 filed May 11, 1990 (hereinafter the "Copending Application"). It should be appreciated that the catheter body can comprise different parts, as for example, an elongated tube and a balloon, opened at both ends, with the balloon attached by both of its neck portions at opposite ends of the balloon to two axially spaced locations on the elongated tube. The latter structure is described in my U.S. Pat. No. 4,820,349 and published European Application 0274411 (Jul. 13, 1988). Alternatively, where the balloon is formed with one closed end so as to form the catheter tip 6, the neck portion provided at its open end can be secured to an appropriate location of the elongated tube. In the case where the balloon is separate from the catheter tube, the balloon can be secured in any manner known in the art, such as with a suitable bonding material Fluid conduits (not shown) are provided so that fluid can be introduced into the balloon so that the latter can be inflated regardless of how much of the balloon 14 is exposed for inflation.

An adjustable sheath 20 is substantially coaxial with the catheter and substantially surrounds catheter body 10, balloon 14 and catheter tip 16. The length of the balloon can vary from very short to as long as (and where the balloon is a single integral piece catheter, defines) the catheter body itself. Catheter body 10, balloon 14 and catheter tip 16, whether made as a single integral piece or as two or more parts, may be made from any conventional high-strength polymeric materials such as polyethylene terephthalate (PET), nylon, polyethylene, polyurethane, fluoropolymers, etc. The balloon can also be made of an elastomeric material, such as latex rubber.

Adjustable sheath 20 is also preferably made from a high-strength polymeric material, but sheath 20 may have different physical requirements than catheter body 10 and in particular balloon 14. More particularly, at least the distal end of sheath 20 must be sufficiently strong and non-compliant so as to be substantially resistant to expansion of any contained portion of the balloon 14. For some applications, such as in treating the prostate, it may be desirable to have all of the sheath 20 be relatively stiff, rigid and non-compliant. In such instances, the rigidity of sheath 20 may be helpful in inserting or introducing the catheter. As should be apparent, in the embodiment where the catheter balloon extends or defines the entire length of the catheter body, sheath 20 must be relatively non-compliant over substantially its entire length. For other applications, such as in balloon angioplasty, it may be desirable to have a sheath 20 that is relatively stiff and non-compliant over most of its length with only its distal end being flexible, trackable and non-compliant in order to restrict balloon expansion.

A variety of approaches can be employed to obtain the desired stiffness and non-compliability for all or a portion of sheath 20. For example, it may be desirable to either uniaxially or biaxially orient the sheath, using conventional methods, in order to strengthen it. The sheath can also be fabricated with thicker and thinner areas, either reinforced or unreinforced with tapers, along its length. The sheath can also be reinforced with a braid or with a high-strength, thin-walled material The entire sheath could also be a very thin, strong and flexible sleeve that can not be pushed forward in use but must be positioned prior to insertion. The sheath can also be in the form of a guide catheter with the balloon catheter adapted to slide within the guide catheter. The sheath can also be provided at the distal end of a relatively stiff, control catheter, with the latter being coaxially mounted on and slidable relative to the balloon catheter. In the latter construction, control of the position of the sheath relative to the balloon can be accomplished at the proximal end by moving the control catheter axially relative to the balloon catheter body so as to move the sheath axially relative to the balloon. The length of the sheath is preferably at least as long as the balloon itself so that the length of balloon desired to be inflated can be adjusted between zero and the entire length of the balloon. Alternatively, the sheath should be sufficiently long so that, at a minimum, it can be adjusted between a position where the exposed balloon portion to be inflated is of minimum length and a position where the exposed balloon portion to be inflated is of a maximum length.

This technology can be modified or tuned to be compatible with virtually any catheter construction including, but not limited to, over the wire catheters, both multi lumen and coaxial designs, and fixed wire catheters where the balloon can be bonded onto the wire or onto a sleeve that is essentially fixed to the wire. Although such wire catheter constructions are not specifically illustrated in the drawings, it is intended that all such balloon catheter designs be within the scope of this invention. Further, it should be understood that the principles of the present invention are not limited to dilatation balloon catheters, but any inflatable devices including any device using a balloon or devices such as described in the Copending Application.

Figure 2:
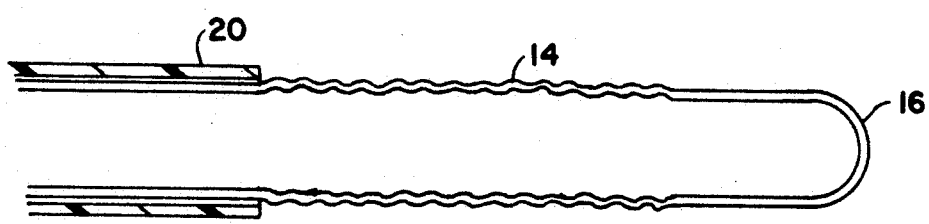
FIG. 2 is a cross-sectional view of the catheter apparatus of FIG. 1, wherein the adjustable sheath has been slid back relative to the balloon toward the proximal end of the apparatus thereby completely exposing the balloon segment.
Figure 3:
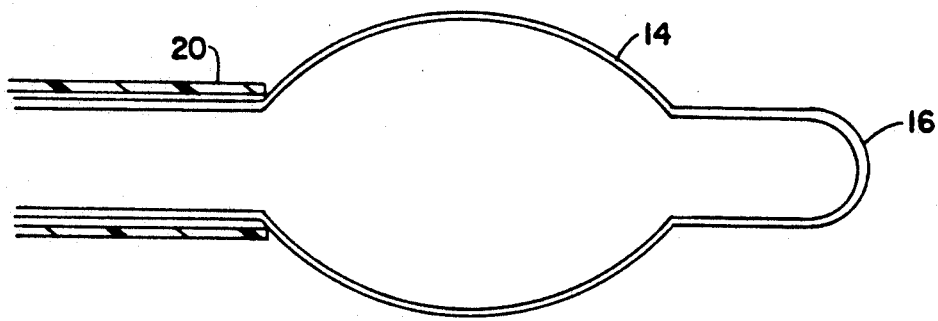
FIG. 3 is a cross-sectional view of the catheter apparatus of FIG. 2, with the balloon segment fully inflated.

FIG. 2 shows a cross-sectional view of the catheter apparatus of FIG. 1 wherein sheath 20 has been slid back toward the proximal end of the apparatus so as to completely expose the inflatable portion of balloon 14, thereby permitting balloon 14 to be completely inflated as shown in FIG. 3. Catheter tip 16 does not inflate under fluid pressure in this embodiment of the invention. As noted above, however, it is within the scope of this invention for tip 16 to be a part of balloon 14, in which case the tip would be fully inflated when sheath 20 is withdrawn as show in FIG. 3.

Figure 4:
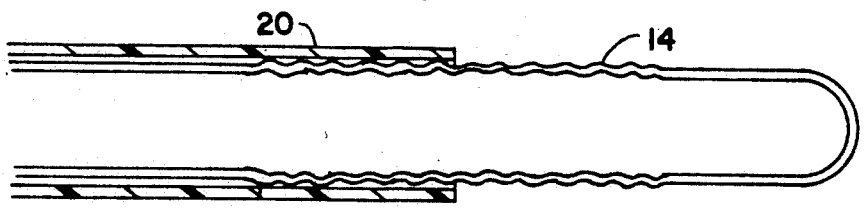
FIG. 4 is another cross-sectional view of the catheter apparatus of FIG. 1, wherein the adjustable sheath has been slid back relative to the balloon segment toward the proximal end of the apparatus so as to expose only a portion of the balloon segment.
Figure 5:
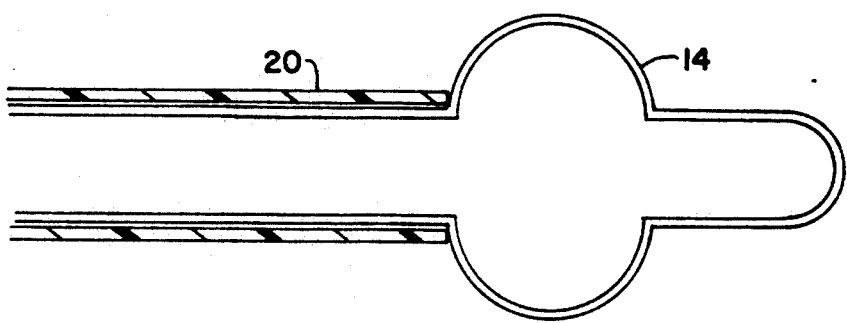
FIG. 5 is a cross-sectional view of the catheter apparatus of FIG. 4 with only the exposed portion of the balloon segment inflated.

FIG. 4 shows another view of the catheter apparatus of FIG. 1, but, in FIG. 4 sheath 20 has been slid back only far enough to expose a portion of balloon 14. This time, when fluid is provided to balloon 14, only the exposed portion of balloon 4 can inflate as shown in FIG. 5, thereby creating a shorter inflated balloon segment as compared with FIG. 3. To the extent there is any tolerance between the internal dimensions of the sheath and the portion of the balloon contained within the sheath, the portion of balloon 14 contained within sheath 20 will stretch and dilate so as to fill sheath 20, but the relatively non-compliant nature of sheath 20 inhibits, and thereby prevents any substantial inflation of this part of the balloon.

It may be preferable that the position of sheath 20 vis-a-vis balloon 14, be firmly fixed, for example by a clamping device (not shown) or other conventional fastening techniques, prior to inflation of the balloon to insure that there is no "creep" during or after inflation tending to uncover more of balloon 14 than originally selected. As shown in FIGS. 4 and 5, about one-half of the length of balloon 14 is exposed and free to inflate. It is within the scope of this invention, however, to vary the position of sheath 20 between exposing essentially all of balloon 14 (FIGS. 2 and 3) to exposing none of balloon 14, and any point inbetween.

The catheter can also include means for visually determining the inflatable portion of the balloon which is disposed beyond the distal end of the adjustable sheath. One such means includes graduated markings on the catheter body. The graduated markings can be provided at the proximal end of the catheter so that the exposed length of balloon can be determined even if the catheter is already in the body. Alternatively, all or at least the distal end of the sheath can be provided with a filler, marking or band made of a material (such as a radiopaque material) visible on X-ray or fluoroscopic viewing to determined the location of the distal end of the sheath and, thus where the proximal end of the inflatable portion of the balloon begins. This marker or band can be used alone, or together with a similar marking, preferably at the distal end of the balloon, shown at the tip of the catheter, so as to identify the inflatable portion of the balloon, in situ, prior to inflation.

After treatment is completed, balloon 14 is deflated, and sheath 20 is preferably slid forward until balloon 14 and tip 16 are once again substantially surrounded by sheath 20 as shown in FIG. 1. It should be appreciated that even if the sheath is not moved relative to the balloon, where only a portion of the balloon is exposed the sheath will help fold the balloon, because the balloon portion under the sheath is already folded so that there is no thick balloon cone to fold down. The catheter apparatus can then be repositioned and utilized for subsequent treatments, as described below, or else it can be withdrawn from the body. During the withdrawal procedure, sheath 20 also helps to ensure proper folding of the balloon.

Figure 6:
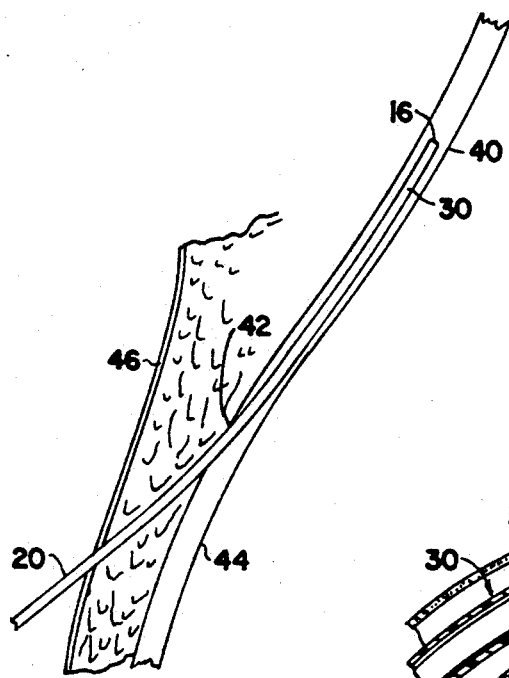
FIG. 6 shows a simplified schematic of the general manner in which a percutaneous insertion is made using the catheter apparatus of this invention.
Figure 7:
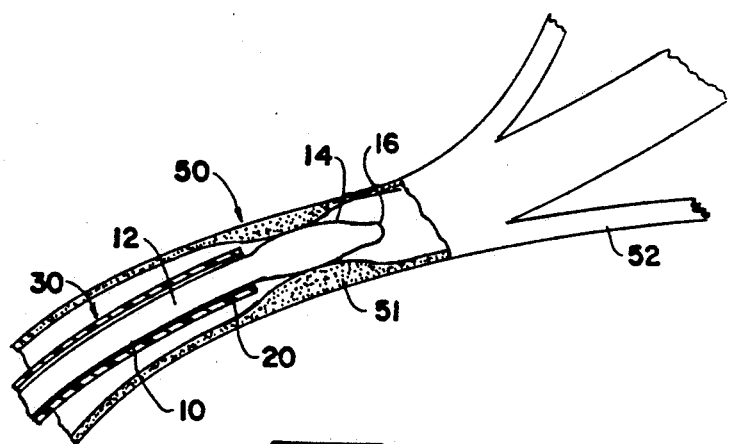
FIG. 7 is a schematic showing how the balloon catheter apparatus of this invention is positioned at a blockage site in a coronary artery.

FIGS. 6 and 7 illustrate one of the many applications of the improved balloon catheter apparatus of this invention.

FIG. 6 is a simplified schematic view illustrating a percutaneous insertion of the catheter apparatus 30 of this invention into an arterial canal, such as into the iliac artery 40 through a puncture 42 in the femoral artery 44. Sheath 20 extends rearwardly from the tip 16 of the catheter, through the puncture 42, formed for example by a hypodermic needle, and extends outwardly through the skin 46.

FIG. 7 is a simplified schematic view illustrating the use of the catheter apparatus 30 of this invention in treating an arterial blockage. As shown in FIG. 6, sheath 20 is inserted into an arterial canal and threaded through the artery to reach a treatment site 50, such as a placque obstruction or stenotic region 51 in coronary artery 52. Catheter body 10 and balloon 14 may already be positioned inside sheath 20 prior to insertion into the artery; or, alternatively, sheath 20 can be used as a guide catheter for inserting body 10 and balloon 14 after sheath 20 has been properly positioned at the treatment site 50.

Unlike the conventional angioplasty procedure, however, in which a guide catheter with a predetermined length balloon is inserted through a body lumen. The balloon size is typically determined before hand, by viewing a fluoroscopic, acoustic or X-ray image of the portion of the body receiving treatment. In the method of this invention where the length of the balloon can be adjusted after the balloon is inserted the sheath can completely cover the balloon when the latter is inserted. Based on the surgeon's previous determination of the size of obstruction or stenotic region 51, the surgeon can then slide sheath 20 rearwardly so as to expose a predetermined length of balloon 14, such length being commensurate with the size of obstruction or stenotic region 51, and can secure sheath 20 at its proximal end to prevent slippage or movement with respect to balloon 14. Balloon 14 is then ready for dilatation with a fluid provided through lumen 12 according to conventional procedures.

Instead of treating all of an obstruction or stenotic region at the same time, the apparatus of this invention also permits a surgeon to gradually open a large obstruction or stenotic region. On the first pass, a relatively small section of balloon 14 would be exposed and inflated. By sliding sheath 20, or advancing the balloon relative to the sheath, larger and larger balloon lengths could be exposed for subsequent dilatations until all of the obstruction or stenotic region is treated.

To treat a second obstruction in the same artery, (a) balloon 14 would be deflated, (b) sheath 20 would be advanced so as to surround balloon 14, or the entire assembly can be advanced, and (c) the catheter apparatus positioned at the new treatment site. Sheath 20 would again be slid rearwardly so as to expose another predetermined length of balloon 14 commensurate with the size of the second obstruction, and the dilatation procedure would be repeated. Alternatively, the entire assembly can be advanced from one position to the next by simply deflating the balloon and moving the assembly with adjusting the sheath relative to the balloon; or where the size of the obstruction is predetermined, the sheath can be adjusted to expose the desired length of balloon, and with the balloon deflated, the distal end of the catheter inserted to its appropriate position so that the exposed portion of the balloon can be inflated. Although the use of the improved balloon catheter apparatus of this invention has been described above in detail with respect to an angioplasty procedure, it will be apparent to those in the field that the subject apparatus could be used in a similar fashion for prostate dilatation and other known applications for balloon catheters, in virtually any body orifice or cavity, including the use of elastomeric balloons for occlusion or diagnostic purposes. All such applications are intended to be within the scope of this invention.

Figure 8:
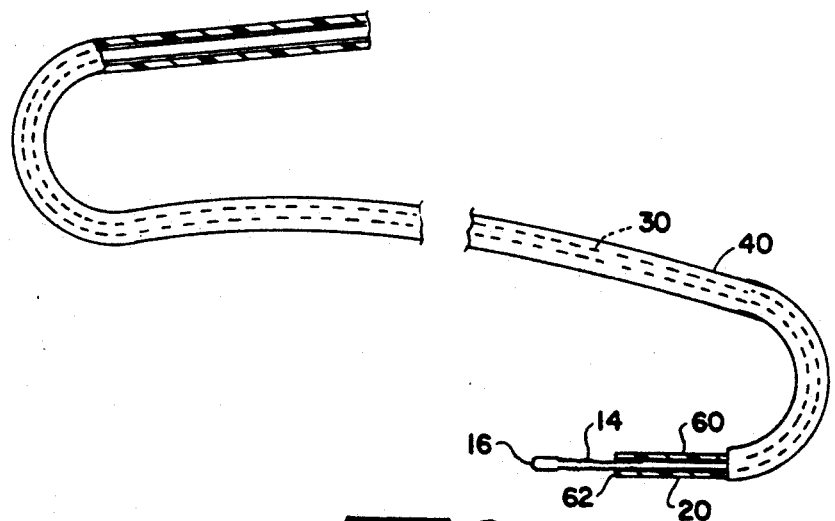
FIG. 8 is a cross-sectional view of an alternative embodiment wherein the adjustable length balloon catheter apparatus of this invention includes a guide catheter, wherein the guide catheter is used as the restricting sheath.

FIG. 8 illustrates an alternative embodiment of this invention wherein the catheter apparatus 30 shown includes the catheter body 10 used with a conventional guide catheter 60, wherein the conventional guide catheter performs its intended function as well as that of the sheath 20 for determining, based on its axial position relative to the balloon, how much of the balloon can be inflated. In this embodiment, guide catheter 60, having an inner lumen large enough to accommodate the catheter body 10, is first inserted into a body cavity or lumen, e.g., an arterial canal 40 shown in FIG. 6, in a conventional fashion and advanced to the intended treatment site. Catheter body 10 is then threaded through the guide catheter 60 until balloon 14 and tip 16, advances beyond the open, distal end 62 of guide catheter 60 to the treatment site 50 as shown in FIG. 7. Then the inner catheter body 10 is slid forwardly (or the guide catheter is retracted relative to the balloon) so as to expose a predetermined length of balloon 14.

Figure 9:
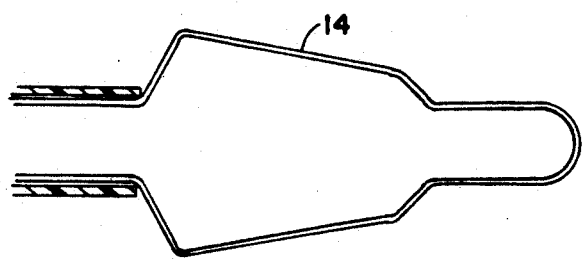
FIG. 9 is a cross-sectional view of a balloon catheter provided with a balloon having a cross-sectional dimension which varies along the length of the balloon and made according to the principles of the present invention.

As previously mentioned, the balloon can vary is cross-sectional shape and/or dimensions over is length. FIG. 9 illustrates still another embodiment of this invention wherein the balloon 14 is tapered, e.g., the cross-sectional radius decreases from its proximal end to its distal end. The sheath 20 can be used to determine how much of the balloon will be inflated, and therefore, the maximum diameter of the inflated balloon.

The foregoing provides an improved balloon dilatation catheter apparatus wherein the length or the shape of the inflated portion of the balloon 14 can be readily adjusted to suit different applications. The coaxial adjustable sheath means 20 is dimensioned so as to fit over and around and slide relative to the balloon when the balloon is not inflated so as to determine which portion of the balloon will inflate when fluid is provided to the balloon. By manipulating the sheath 20 the length and shape of the balloon can be determined. The adjustment can be accomplished before the procedure is commenced, or in situ while the procedure is in process. Means can be provided for visually determining the length of the portion of the balloon that will inflate. The sheath means has sufficient flexibility and tractability to facilitate guiding the sheath means to the treatment site, and resistance to inflation and rupture. The apparatus provides a easy way to adjust the length or shape of the inflated portion of the balloon of a balloon catheter such that a single catheter can be used for multiple applications in treating sites of varying sizes and locations.

Since certain changes may be made in the above-described apparatuses and processes without departing from the scope of the invention herein involved, it is intended that all matter contained in the above description shall be interpreted in an illustrative and not in a limiting sense.

Having described the invention, what I claim is:

1. A method of treating obstructed regions of bodily passageways, said method comprising the following steps:

(a) inserting into a bodily passageway a catheter apparatus comprising catheter means including a balloon, and adjustable sheath means surrounding said balloon, said sheath means being substantially non-compliant and resistant to expansion of said balloon;

(b) positioning said catheter apparatus in said passageway such that said balloon and said sheath means are located within a first obstructed region;

(c) adjusting said sheath means so as to expose a first portion of said balloon, said first portion being less than the length of the balloon;

(d) dilating said balloon to treat at least a first section of said first stenotic region;

(e) deflating said balloon;

(f) adjusting said sheath means so as to cover said balloon;

(g) repositioning said catheter apparatus in said passageway such that said sheath means is located within a second obstructed region;

(h) adjusting said sheath means and balloon relative to one another so as to expose a second portion of said balloon, said second portion being less than the length of the balloon; and (i) dilating said balloon to treat at least a first section of said second obstructed region.

2. The method according to claim 1, further comprising the steps of:

(j) deflating said balloon;

(k) adjusting said sheath means and balloon relative to one another so as to cover said balloon; and (l) withdrawing said catheter apparatus from said passageway.

3. The method according to claim 1, further comprising the steps of:

(j) deflating said balloon;

(k) adjusting said sheath means so as to expose a third portion of said balloon, said third portion being less than the length of the balloon but greater than said second portion;

(l) inflating said balloon to treat a larger section of said second stenotic region; and (m) repeating the foregoing steps with progressively longer exposed portions of said balloon until all of said second obstructed region has been treated.

4. The method according to claim 1, wherein said sheath means is substantially coaxial with said catheter means.

5. The method according to claim 1 further including the step of controlling the position of said sheath means relative to said balloon by manipulating a tube having a distal end connected to said sheath means and a proximal end for controlling the position of said sheath means relative to said balloon.

6. The method according to claim 1, wherein said sheath means comprises a high-strength material having a property of being substantially non-compliant and resistant to expansion of the enclosed portion of said balloon when said balloon is in an inflated state.

7. The method according to claim 6, wherein said high-strength material is selected from the group consisting essentially of polyethylene terephthalate, polyamide, polyethylene, polyurethane and fluoropolymers.

8. The method according to claim 6, wherein said sheath means has been strengthened through uniaxial or biaxial orientation.

9. The method according to claim 6, wherein said sheath means is reinforced with braiding or a high-strength, thin-walled material.

10. The method according to claim 1, wherein the cross-sectional dimensions of said balloon varies along the axial length of said balloon.

11. The method according to claim 1, further comprising the step of detecting indicia on the internal end of said catheter apparatus in order to expose a predetermined length of said balloon prior to dilating said balloon.

12. The method according to claim 11, wherein said indicia for ascertaining the length of the exposed portion of said balloon includes at least a marking on the distal end of said sheath means and the distal end of said balloon.

13. The method according to claim 12, wherein each said marking is radiopaque.

14. The method according to claim 1, further comprising the steps of repeating said repositioning, adjusting and dilating steps in order to treat additional stenotic regions in said passageway.

15. The method according to claim 1, further comprising the step of visualizing indicia on the external end of said catheter apparatus in order to expose a predetermined length of said balloon prior to dilating said balloon.

16. The method according to claim 15, wherein said indicia for visually ascertaining the length of the exposed portion of said balloon includes marking means on at least said sheath means or on the catheter means.

17. The method according to claim 1, further comprising the step of using a guide catheter to assist in inserting said balloon dilatation catheter apparatus into said passageway.

* * * * *